United States Patent
Kyakuno

(10) Patent No.: US 12,265,051 B2
(45) Date of Patent: Apr. 1, 2025

(54) RESIDUAL CHLORINE METER, CONTROL METHOD THEREOF, AND CHLORINE METER SYSTEM

(71) Applicant: Yokogawa Electric Corporation, Tokyo (JP)

(72) Inventor: Toshihiko Kyakuno, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 0 days.

(21) Appl. No.: 18/090,169

(22) Filed: Dec. 28, 2022

(65) Prior Publication Data

US 2023/0213472 A1 Jul. 6, 2023

(30) Foreign Application Priority Data

Jan. 6, 2022 (JP) ................................. 2022-001233

(51) Int. Cl.
*G01N 27/333* (2006.01)
*G01N 33/18* (2006.01)

(52) U.S. Cl.
CPC ........... *G01N 27/333* (2013.01); *G01N 33/18* (2013.01)

(58) Field of Classification Search
CPC .. G01N 27/333; G01N 27/38; G01N 27/4168; G01N 33/18
See application file for complete search history.

(56) References Cited

U.S. PATENT DOCUMENTS 5,460,710 A 10/1995 Williams et al.

FOREIGN PATENT DOCUMENTS

| JP | 59-228159 A | | 12/1984 |
|---|---|---|---|
| JP | 60-205345 A | | 10/1985 |
| JP | 6-508432 A | | 9/1994 |
| JP | H1175349 A | * | 3/1999 |
| JP | 2008-164408 A | | 7/2008 |
| JP | 2009168694 A | * | 7/2009 |
| JP | 2010045953 A | * | 2/2010 |
| JP | 2010185678 A | * | 8/2010 |
| JP | 5251573 B2 | * | 7/2013 |

(Continued)

OTHER PUBLICATIONS

Mihashi et al. English translation of JP-2016080573-A, 2016 (Year: 2016).*

(Continued)

*Primary Examiner* — Brian W Cohen
*Assistant Examiner* — Shizhi Qian
(74) *Attorney, Agent, or Firm* — RANKIN, HILL & CLARK LLP

(57) ABSTRACT

A residual chlorine meter for measuring the concentration of residual chlorine in sample water includes an indicator electrode and a counter electrode to be immersed in the sample water and a controller that measures the concentration of residual chlorine in the sample water based on a diffusion current flowing between the indicator electrode and the counter electrode in a case in which a voltage is applied between the indicator electrode and the counter electrode. The controller detects a degree of deterioration of a replaceable component of the residual chlorine meter based on a motor current, flowing through a motor that rotates the indicator electrode in the sample water, and/or the diffusion current.

8 Claims, 6 Drawing Sheets

(56) References Cited

FOREIGN PATENT DOCUMENTS

| JP | 2016080573 | A | * | 5/2016 |
| JP | 2016191605 | A | * | 11/2016 |
| WO | WO-2020045285 | A1 | * | 3/2020 |

OTHER PUBLICATIONS

Ishikawa et al. English translation of JP-2010045953-A, 2010 (Year: 2010).*
Hirata et al., English translation of JPH1175349A, 1999 (Year: 1999).*
Ishikawa et al., English translation of JP5251573B2, 2013 (Year: 2013).*
Japanese Office Action (JPOA) dated Jan. 9, 2024 for Japanese Patent Application No. 2022-001233; English translation.

* cited by examiner

RESIDUAL CHLORINE METER, CONTROL METHOD THEREOF, AND CHLORINE METER SYSTEM

CROSS-REFERENCE TO RELATED APPLICATION

The present application claims priority to Japanese Patent Application No. 2022-001233 filed on Jan. 6, 2022, the entire contents of which are incorporated herein by reference.

TECHNICAL FIELD

The present disclosure relates to a residual chlorine meter, a control method thereof, and a chlorine meter system.

BACKGROUND

Patent literature (PTL) 1 describes a residual chlorine meter that measures residual chlorine in water using a polarograph method.

Citation List

Patent Literature
  PTL 1: JP 2008-164408 A

SUMMARY

A residual chlorine meter according to an embodiment is a residual chlorine meter for measuring a concentration of residual chlorine in sample water, the residual chlorine meter including an indicator electrode and a counter electrode to be immersed in the sample water, and a controller configured to measure a concentration of residual chlorine in the sample water based on a diffusion current flowing between the indicator electrode and the counter electrode in a case in which a voltage is applied between the indicator electrode and the counter electrode, wherein the controller is configured to detect a degree of deterioration of a replaceable component of the residual chlorine meter based on a motor current, flowing through a motor that rotates the indicator electrode in the sample water, and/or the diffusion current.

A chlorine meter system according to an embodiment includes a residual chlorine meter for measuring a concentration of residual chlorine in sample water and an information processing apparatus, the residual chlorine meter including an indicator electrode and a counter electrode to be immersed in the sample water, and a controller configured to measure a concentration of residual chlorine in the sample water based on a diffusion current flowing between the indicator electrode and the counter electrode in a case in which a voltage is applied between the indicator electrode and the counter electrode, the information processing apparatus being configured to communicate with the residual chlorine meter, wherein the information processing apparatus is configured to detect a degree of deterioration of a replaceable component of the residual chlorine meter based on a motor current, flowing through a motor that rotates the indicator electrode in the sample water, and/or the diffusion current.

A control method for a residual chlorine meter according to an embodiment is a control method for a residual chlorine meter that includes an indicator electrode and a counter electrode to be immersed in sample water, and a controller configured to measure a concentration of residual chlorine in the sample water based on a diffusion current flowing between the indicator electrode and the counter electrode in a case in which a voltage is applied between the indicator electrode and the counter electrode, the control method including detecting, by the controller, a degree of deterioration of a replaceable component of the residual chlorine meter based on a motor current, flowing through a motor that rotates the indicator electrode in the sample water, and/or the diffusion current.

BRIEF DESCRIPTION OF THE DRAWINGS

In the accompanying drawings.

DETAILED DESCRIPTION

Figure 1:
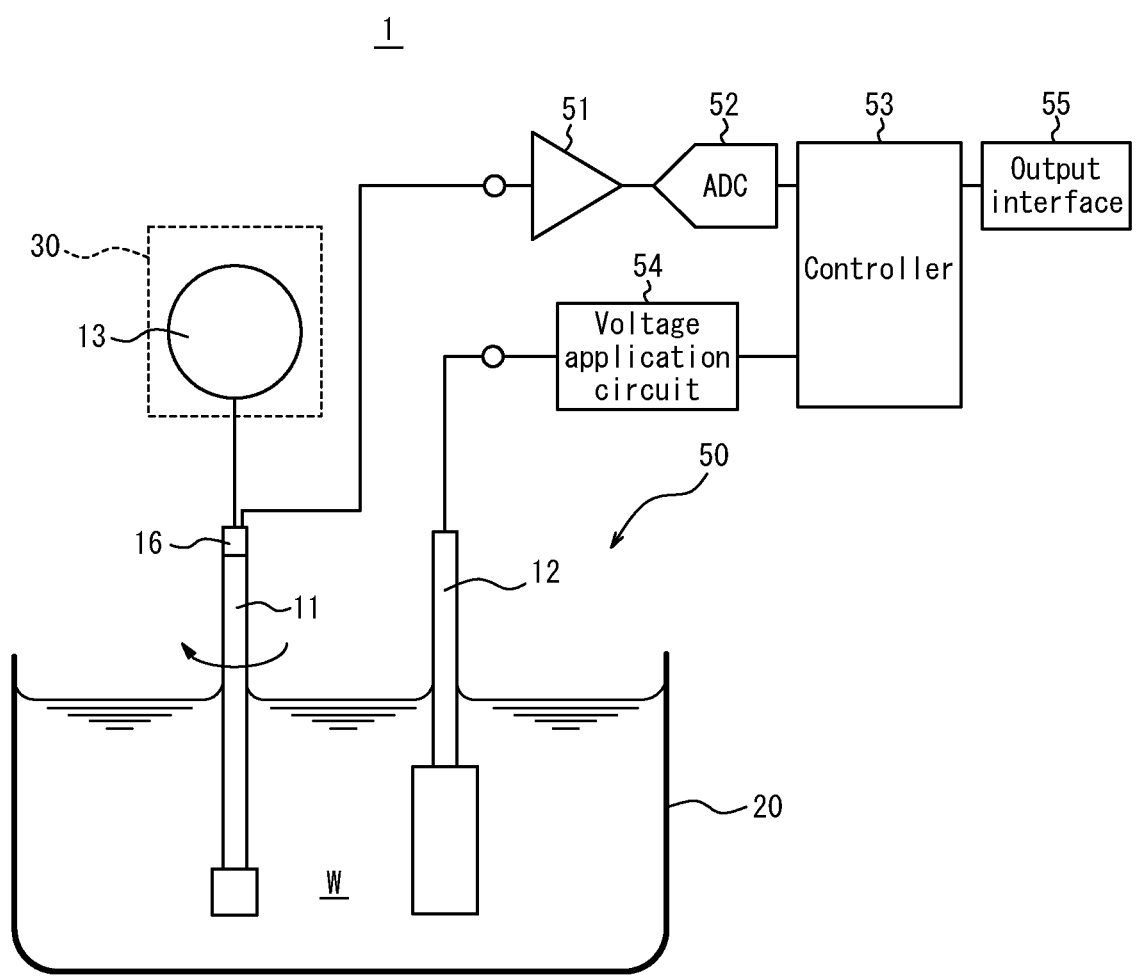
FIG. 1 is a diagram illustrating an example configuration of a residual chlorine meter according to an embodiment.

Replaceable components of residual chlorine meters, such as electrodes and motors, deteriorate with long-term use and thus need to be replaced periodically. In a known configuration, users replace the replaceable components of the residual chlorine meter according to a replacement cycle or the like recommended by the manufacturer. However, since the degree of deterioration of the replaceable components varies depending on the use environment, known configurations have room for improvement with regard to the timing of replacement of the replaceable components.

It would be helpful to provide a residual chlorine meter, a control method thereof, and a chlorine meter system that enable the replacement of replaceable components at a more appropriate timing.

A residual chlorine meter according to an embodiment is a residual chlorine meter for measuring a concentration of residual chlorine in sample water and includes an indicator electrode and a counter electrode to be immersed in the sample water, and a controller configured to measure a concentration of residual chlorine in the sample water based on a diffusion current flowing between the indicator electrode and the counter electrode in a case in which a voltage is applied between the indicator electrode and the counter electrode, wherein the controller is configured to detect a degree of deterioration of a replaceable component of the residual chlorine meter based on a motor current, flowing through a motor that rotates the indicator electrode in the sample water, and/or the diffusion current.

Since the residual chlorine meter thus detects the degree of deterioration of the replaceable component based on the motor current and/or the diffusion current, the user can replace the replaceable component at a more appropriate timing according to the degree of deterioration.

In the residual chlorine meter according to an embodiment, the controller is configured to perform AC-type analysis, which is signal analysis to detect periodic fluctuations, on the motor current and/or the diffusion current, and detect the degree of deterioration of the replaceable component of the residual chlorine meter by comparing a result of the AC-type analysis performed on the motor current and/or the diffusion current with a result of the AC-type analysis on a sample signal acquired in advance.

Since the residual chlorine meter thus detects the degree of deterioration of the replaceable component by performing AC-type analysis on the motor current and/or the diffusion current, the residual chlorine meter can appropriately detect deterioration of the replaceable component, which manifests as periodic fluctuations in the motor current or the diffusion current.

In the residual chlorine meter according to an embodiment, the controller is configured to perform DC-type analysis, which is signal analysis to detect an overall trend in values, on the motor current and/or the diffusion current, and detect the degree of deterioration of the replaceable component of the residual chlorine meter by comparing a result of the DC-type analysis performed on the motor current and/or the diffusion current with a result of the DC-type analysis on a sample signal acquired in advance.

Since the residual chlorine meter thus detects the degree of deterioration of the replaceable component by performing DC-type analysis on the motor current and/or the diffusion current, the residual chlorine meter can appropriately detect deterioration of the replaceable component, which manifests as overall fluctuations in the motor current or the diffusion current.

In the residual chlorine meter according to an embodiment, the replaceable component is the motor, an electrode of the indicator electrode, or a sliding contact for extracting the diffusion current from the indicator electrode. The residual chlorine meter is therefore capable of detecting deterioration with respect to the motor, the electrode of the indicator electrode, and the sliding contact.

In the residual chlorine meter according to an embodiment, the controller is configured to determine whether the replaceable component should be replaced based on the detected degree of deterioration and present a result of determining whether the replaceable component should be replaced to a user. Accordingly, the user can easily grasp whether the replaceable component needs to be replaced.

A chlorine meter system according to an embodiment includes a residual chlorine meter for measuring a concentration of residual chlorine in sample water and an information processing apparatus, the residual chlorine meter including an indicator electrode and a counter electrode to be immersed in the sample water, and a controller configured to measure a concentration of residual chlorine in the sample water based on a diffusion current flowing between the indicator electrode and the counter electrode in a case in which a voltage is applied between the indicator electrode and the counter electrode, the information processing apparatus being configured to communicate with the residual chlorine meter, wherein the information processing apparatus is configured to detect a degree of deterioration of a replaceable component of the residual chlorine meter based on a motor current, flowing through a motor that rotates the indicator electrode in the sample water, and/or the diffusion current.

Since the information processing apparatus thus detects the degree of deterioration of the replaceable component based on the motor current and/or the diffusion current, the user can replace the replaceable component at a more appropriate timing according to the degree of deterioration, even if the residual chlorine meter is not equipped with a data analysis capability.

A control method for a residual chlorine meter according to an embodiment is a control method for a residual chlorine meter that includes an indicator electrode and a counter electrode to be immersed in sample water, and a controller configured to measure a concentration of residual chlorine in the sample water based on a diffusion current flowing between the indicator electrode and the counter electrode in a case in which a voltage is applied between the indicator electrode and the counter electrode, the control method including detecting, by the controller, a degree of deterioration of a replaceable component of the residual chlorine meter based on a motor current, flowing through a motor that rotates the indicator electrode in the sample water, and/or the diffusion current.

Since the residual chlorine meter thus detects the degree of deterioration of the replaceable component based on the motor current and/or the diffusion current, the user can replace the replaceable component at a more appropriate timing according to the degree of deterioration.

According to an embodiment of the present disclosure, a replaceable component of a residual chlorine meter can be replaced at a more appropriate timing.

Comparative Example

A residual chlorine meter is an apparatus for measuring the concentration of residual chlorine (also called "residual salt concentration") included in sample water such as tap water. Residual chlorine refers to a combination of free residual chlorine and bound residual chlorine present in the sample water. When two electrodes, referred to as an indicator electrode and a counter electrode (comparison electrode), are immersed in the sample water and a voltage is applied between the indicator electrode and the counter electrode with the indicator electrode side as the cathode, an electric field reduction reaction of chlorine, which is a substance to be electrolyzed, occurs on the surface of the indicator electrode, and an electric current flows between the indicator electrode and the counter electrode.

When voltage is applied between the indicator electrode and the counter electrode, a constant diffusion layer with concentration polarization is formed in the vicinity of the indicator electrode. In this state, the electrolytic reduction current is proportional to the diffusion rate. The diffusion rate is proportional to the residual chlorine concentration in the sample water. Therefore, the residual chlorine meter can measure the concentration of residual chlorine in the sample water by measuring the current (diffusion current) in the state in which the diffusion layer is formed. The concentration measurement method based on this measurement principle is called the polarograph method.

In such chlorine concentration measurement, it is important to keep the thickness of the diffusion layer constant to obtain stable proportionality between the chlorine concentration and the diffusion current. Therefore, to keep the thickness of the diffusion layer constant, the residual chlorine meter uses a motor to rotate the indicator electrode at a constant speed during measurement.

Replaceable components of residual chlorine meters, such as electrodes and motors, deteriorate with long-term use and thus need to be replaced periodically. In the chlorine concentration meter according to the comparative example, users replace the replaceable components of the residual chlorine meter according to a replacement cycle or the like recommended by the manufacturer of the chlorine concentration meter. However, the degree of deterioration of the replaceable components varies depending on the use environment. Therefore, in a known configuration, continued use of the replaceable components that have deteriorated and need to be replaced may cause problems, such as degradation of the performance of the product. Replacement of components that do not yet need to be replaced in the known configuration could also result in unnecessary costs.

It would be helpful to enable the replacement of replaceable components in a residual chlorine meter at a more appropriate timing.

Embodiments

Embodiments of the present disclosure are now described with reference to the drawings. Portions having an identical configuration or function in the drawings are labeled with the same reference signs. In the explanation of the embodiments, a redundant description of identical portions may be omitted or simplified as appropriate.

First Embodiment

A residual chlorine meter according to the present disclosure measures the current or diffusion current flowing through the motor that rotates the indicator electrode and detects the degree of deterioration of a replaceable component based on the current. The residual chlorine meter notifies the user in a case in which the replaceable component is in a state requiring replacement according to the detected degree of deterioration, thereby enabling the user to replace the replaceable component at the appropriate timing.

FIG. 1 is a diagram illustrating an example configuration of a residual chlorine meter 1 according to an embodiment. The residual chlorine meter 1 includes an indicator electrode 11, a counter electrode (comparison electrode) 12, a motor drive unit 30 including a motor 13, a sliding contact 16, a current to voltage conversion circuit 51, an analog to digital converter 52, a controller 53, a voltage application circuit 54, and an output interface 55.

The indicator electrode 11 and the counter electrode 12 are electrodes. The indicator electrode 11 and the counter electrode 12 are immersed in sample water W, such as tap water, stored inside walls 20 forming part of a measurement tank 50. A voltage is applied between the indicator electrode 11 and the counter electrode 12 based on control by the controller 53.

The motor 13 is the power source that rotates the indicator electrode 11 at a constant speed during measurement of the residual chlorine concentration. The motor 13 has any appropriate configuration that converts electricity into power to rotate the indicator electrode 11. The configuration of the motor drive unit 30 that drives the motor 13 is described below with reference to FIG. 3.

The sliding contact 16 is an electrical transmission mechanism that extracts the diffusion current when an electrical connection between the indicator electrode 11 and the current to voltage conversion circuit 51 is maintained while the indicator electrode 11 is being rotated by the motor 13. Since the indicator electrode 11 is constantly rotating during measurement, the residual chlorine meter 1 detects the diffusion current by extracting, from the sliding contact 16, the current flowing through the indicator electrode 11, which is a rotating body. The residual chlorine meter 1 according to the present embodiment includes the sliding contact 16 that employs a sliding method with a brush and rotor as an electrical contact device (contact) for extracting signals from the indicator electrode 11, but the residual chlorine meter 1 is not limited to this configuration as long as it can extract signals from the indicator electrode 11. For example, the electrical contact device may be configured to transmit electricity or electric signals between the rotating body (indicator electrode 11) and a contact in a resting state via a metal ball in a storage compartment. The electrical contact device may use any appropriate mechanism to extract current or voltage signals from the indicator electrode 11, which is a rotating body. The electrical contact device may also use a mechanism that utilizes a liquid metal such as mercury. The sliding contact 16 may be configured by a metal alloy with excellent wear resistance and corrosion resistance. Alternatively, the sliding contact 16 may be made of a metal resistant to corrosion, such as titanium, platinum, gold, silver, or stainless steel. The value of the diffusion current extracted by the sliding contact 16 is transmitted to the controller 41, described below.

The current to voltage conversion circuit 51 is a circuit that converts the diffusion current acquired via the sliding contact 16 into a voltage. The current to voltage conversion circuit 51, described below with reference to FIG. 3, may have a configuration such as resistors 33 to 35, 37 and a comparator (operational amplifier) 36. The analog to digital converter 52 converts the voltage corresponding to the diffusion current from an analog signal to a digital signal. The digital signal is outputted to the controller 53.

The controller 53 includes one or more processors. The "processor" in an embodiment is a general purpose processor, such as a central processing unit (CPU), or a dedicated processor specialized for particular processing, but these examples are not limiting. The controller 53 is communicably connected to each of the components for measuring the diffusion current and controls the operation of the residual chlorine meter 1 with respect to the measurement of the diffusion current. The voltage application circuit 54 is a circuit that, based on control by the controller 53, generates a potential difference between the indicator electrode 11 and the counter electrode 12, with the indicator electrode 11 side as the cathode. The voltage application circuit 54 acts as a power supply that generates a potential difference between the indicator electrode 11 and the counter electrode 12. The output interface 55 includes one or more output interfaces that output information to the user to notify the user. For example, the output interface 55 may be a display that outputs information as images, a speaker that outputs information as sound, or the like, but these examples are not limiting. The controller 53, the voltage application circuit 54, and the output interface 55 may have a shared configuration with the controller 41, the power supply 31, and the output interface 45 of the motor drive unit 30, described below.

Figure 2:
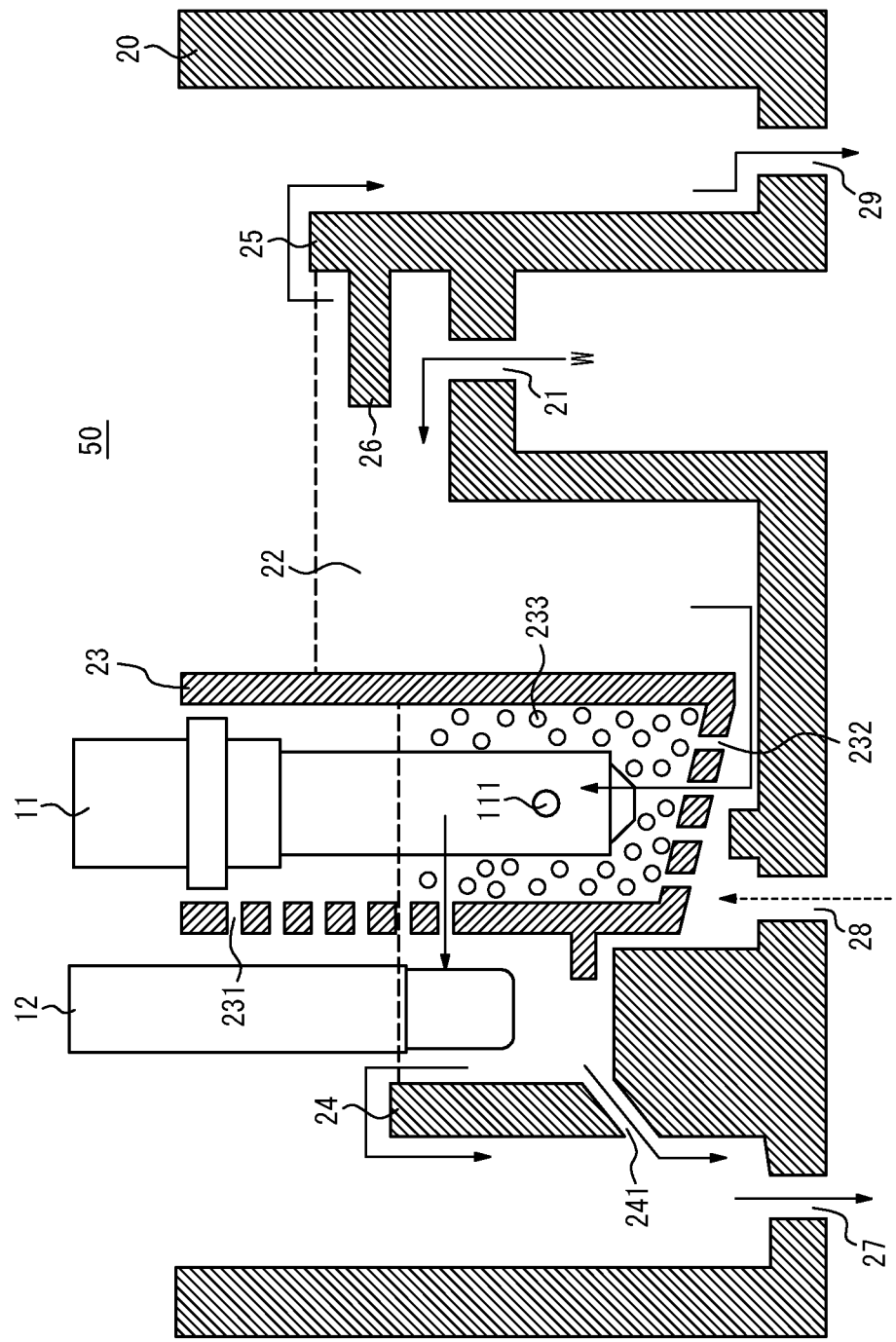
FIG. 2 is a diagram illustrating an example configuration of a measurement tank in FIG. 1.

FIG. 2 is a diagram illustrating an example configuration of the measurement tank 50 of FIG. 1. The measurement tank 50 includes the walls 20, a water inlet 21, a mixing tank 22, a bead case 23, overflow weirs 24, 25, a buffer plate 26, a drain 27, a backwash port 28, and a drain 29. A bead case 23 filled with beads 233 is provided in the mixing tank 22. The indicator electrode 11 is installed in the bead case 23 and is rotated by the motor 13. The counter electrode 12 is installed inside the mixing tank 22, outside the bead case 23.

The sample water W is injected from the water inlet 21 into the mixing tank 22. The sample water W passes through the mixing tank 22, the bead case 23, the indicator electrode 11, the counter electrode 12, and the overflow weirs 24, 25 and is discharged through the drains 27, 29. The overflow weirs 24, 25 and the buffer plate 26, provided in the vicinity of the water inlet 21, make it possible to send the sample water W to the indicator electrode 11 at a nearly constant flow rate, regardless of the flow range of the sample water W injected from the water inlet 21. The sample water W may be injected into the mixing tank 22 from the backwash port 28 instead of the water inlet 21. Dirt and the like that has accumulated at a particular location in the measurement tank 50 may be cleaned by the periodic injection of cleaning water, which has passed through a cleaning filter, from the separately provided backwash port 28 instead of the normally used water inlet 21.

The indicator electrode 11 includes an electrode 111 and is used to measure the diffusion current that is proportional to the residual chlorine concentration. If physical or electrical dirt or the like adheres to the indicator electrode 11, the correct value of the diffusion current cannot be measured. The indicator electrode 11 therefore needs to be cleaned constantly. By rotating the indicator electrode 11 inside the bead case 23 filled with small beads 233, the residual chlorine meter 1 according to the present embodiment polishes the surface of the indicator electrode 11 with the beads 233 to keep the indicator electrode 11 constantly cleaned. This prevents adhesion, to the electrode 111, of an iron component, manganese component, or the like contained in the sample water W and prevents a decrease in the sensitivity of the indicator electrode 11. Corrosion of the electrode 111 of the indicator electrode 11 can also be prevented by forming the electrode 111 of the indicator electrode 11 from a material that is resistant to chemical corrosion, such as gold, titanium, platinum, silver, or stainless steel. The beads 233 are formed from ceramic, for example, but may be formed from any material capable of polishing the surface of the electrode 111. For example, the beads 233 may be formed from glass, any appropriate metal, sand, walnuts, or the like. The bead case 23 may include numerous side holes 231 and bottom holes 232 that are smaller than the beads 233 and allow the sample water W to flow in and out of the bead case 23.

The counter electrode 12 may, for example, be formed from silver. In a case in which the counter electrode 12 is formed from silver, a hole 241 may be provided in the overflow weir 24. The hole 241 is used to discharge stagnant water in the mixing tank 22 when the sample water W is no longer flowing, thereby exposing the counter electrode 12 from the water to prevent the indicator electrode 11 from being silver plated.

Figure 3:
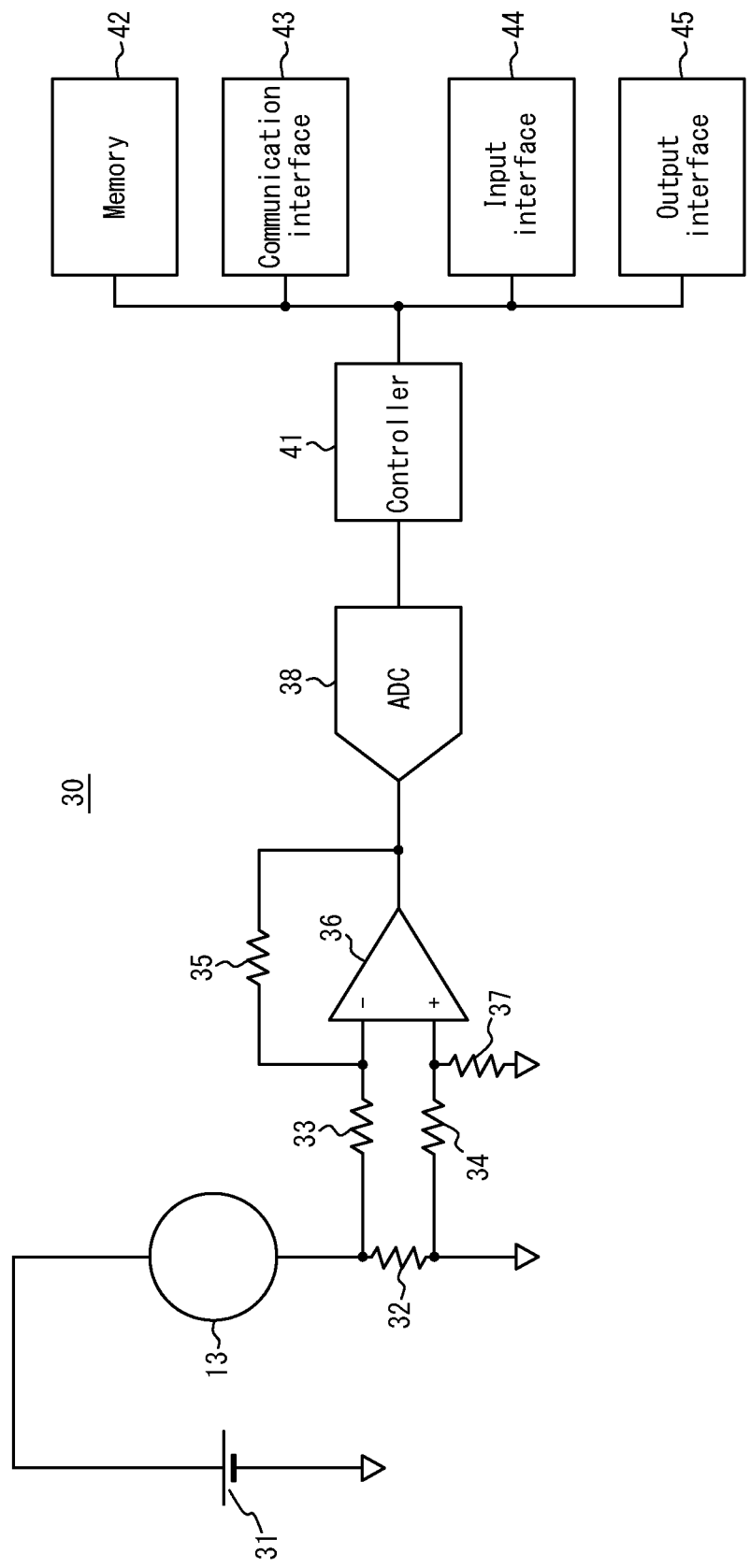
FIG. 3 is a circuit diagram illustrating an example configuration of a motor drive unit in FIG. 1.

FIG. 3 is a circuit diagram illustrating an example configuration of the motor drive unit 30 in FIG. 1. The motor drive unit 30 includes the motor 13, a power supply 31, resistors 32 to 35, a comparator 36, a resistor 37, an analog to digital converter 38, a controller 41, a memory 42, a communication interface 43, an input interface 44, and an output interface 45.

The motor 13 rotates the indicator electrode 11 within the bead case 23. The motor 13 may, for example, by implemented by a stepper motor. The motor 13 may, for example, rotate the indicator electrode 11 at a rate of 10 revolutions per second. The motor 13 is a DC motor in the example below but may also be an AC motor.

The power supply 31 provides electric power for driving the motor 13. The power supply 31 may be the same as the voltage application circuit 54 or may be configured to transform or otherwise convert a power supply shared with the voltage application circuit 54.

The resistor 32 is a resistor for measuring the current flowing through the motor 13. The resistors 33 to 35, 37 and the comparator (operational amplifier) 36 are a current to voltage conversion circuit that converts the current flowing through the motor 13 into a voltage. The analog to digital converter 38 converts the voltage corresponding to the current flowing through the motor 13 from an analog signal to a digital signal. The digital signal is outputted to the controller 41.

The controller 41 includes one or more processors. The "processor" in an embodiment is a general purpose processor, such as a CPU, or a dedicated processor specialized for particular processing, but these examples are not limiting. The controller 41 is communicably connected with each component of the residual chlorine meter 1 and controls operations of the residual chlorine meter 1 with respect to the motor 13. The controller 41 may have the same configuration as the controller 53 of FIG. 1 and may acquire the value of the diffusion current extracted by the sliding contact 16.

The memory 42 includes any storage module, such as a hard disk drive (HDD), a solid state drive (SSD), a read-only memory (ROM), an electrically erasable programmable read-only memory (EEPROM), and a random access memory (RAM). The memory 42 may, for example, function as a main memory, an auxiliary memory, or a cache memory. The memory 42 stores any information used for operations of the residual chlorine meter 1 or resulting from operations of the residual chlorine meter 1. For example, the memory 42 may store various programs, various information such as data on the current flowing through the motor 13 and data on the diffusion current, and the like. The memory 42 is not limited to being internal to the residual chlorine meter 1 and may be an external database or an external storage module connected through a digital input/output port or the like, such as a universal serial bus (USB).

The communication interface 43 includes any appropriate communication module capable of connecting and communicating with other apparatuses, such as the information processing apparatus 2, described below. The communication interface 43 may further include a communication control module for controlling communication with other apparatuses and a storage module for storing communication data, such as identification information, necessary for communicating with other apparatuses.

The input interface 44 includes one or more input interfaces that receive a user input operation and acquire input information based on the user operation. For example, the input interface 44 may be physical keys, capacitive keys, a pointing device, a touchscreen integrally provided with a display of the output interface 45, a microphone that receives audio input, or the like, but is not limited to these.

The output interface 45 includes one or more output interfaces that output information to the user to notify the user. For example, the output interface 45 may be a display that outputs information as images, a speaker that outputs information as sound, or the like, but these examples are not limiting. As described above, the output interface 45 may share a common configuration with the output interface 55.

The functions of the motor drive unit 30 or the residual chlorine meter 1 can be implemented by the processor included in the controller 41 executing a computer program (program) that can be used to perform the deterioration detection according to the present embodiment. That is, at least a portion of the functions of the motor drive unit 30 or the residual chlorine meter 1 can be implemented by software. The computer program causes a computer to execute the processing of the steps included in the operations of the motor drive unit 30 or the residual chlorine meter 1 to implement the functions corresponding to the processing of the steps. That is, the computer program is a program for causing a computer to function as the motor drive unit 30 or the residual chlorine meter 1 according to the present embodiment.

The motor drive unit 30 may have a different configuration from the one illustrated in FIG. 3 as long as the controller 41 can acquire the current signal flowing through the motor 13. In other words, any detection method for the current flowing through the motor 13 is acceptable. For example, if the current signal can be acquired using a current monitoring function of a motor driver integrated circuit (IC), the controller 41 may acquire the current signal directly from the motor driver IC. In this case, the motor drive unit 30 need not include the resistor 32, the resistors 33 to 35 and 37, the comparator 36, and the analog to digital converter 38 for current detection. A portion or all of the functions of the controller 41, the memory 42, the communication interface 43, the input interface 44, and the output interface 45 may be implemented by a dedicated circuit included in the controller 41. In other words, a portion or all of the functions of the motor drive unit 30 or the residual chlorine meter 1 may be implemented by hardware. The residual chlorine meter 1 may have any appropriate configuration for the controller 41 to acquire the diffusion current.

As an example, the residual chlorine meter 1 according to the present embodiment detects the degree of deterioration of each replaceable component, i.e., the electrode 111, the sliding contact 16, and the motor 13, based on the current signal or diffusion current flowing through the motor 13 and determines which replaceable component should be replaced according to the detection results. The principle behind this detection and determination process is explained with reference to FIG. 4.

Figure 4:
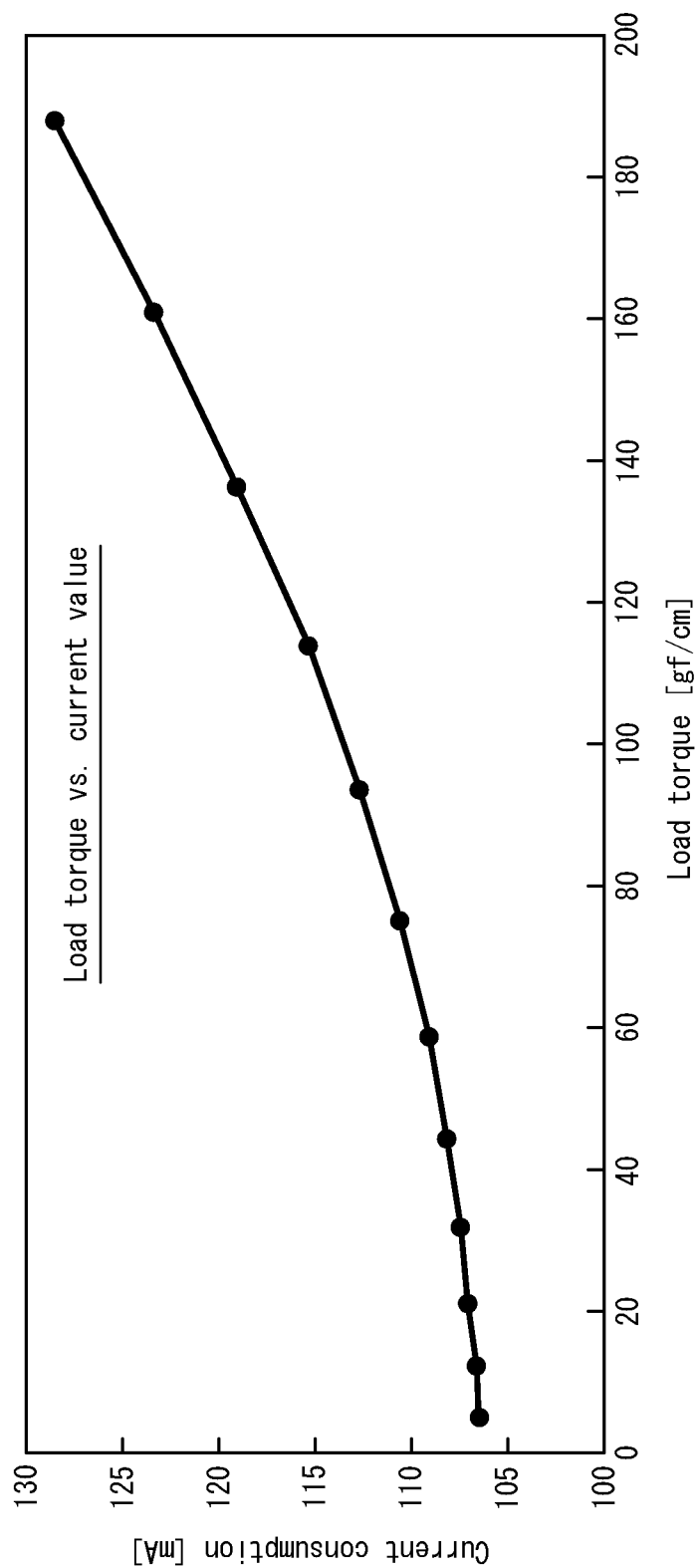
FIG. 4 is a diagram illustrating an example of the correspondence between load torque of a motor and current consumption in the motor.

FIG. 4 is a diagram illustrating an example of the correspondence between load torque of the motor 13 and current consumption in the motor 13. FIG. 4 illustrates an example of the correspondence between the load torque applied to the motor 13 and the current consumed by the motor 13 using a graph. In other words, FIG. 4 is a graph illustrating the change in the current value flowing through the motor 13 when the load torque is increased by gradual application of a brake to the motor 13 rotating with no load. In FIG. 4, the horizontal axis represents the magnitude of the load torque applied to the motor 13, and the vertical axis represents the magnitude of the current flowing through the motor 13. As illustrated in FIG. 4, in general, the load torque and current consumption value have a nonlinear, proportional relationship.

The residual chlorine meter 1 according to the present embodiment uses the fact that the current consumed by the motor 13 and the load torque are closely related. In other words, the residual chlorine meter 1 estimates the magnitude of the load torque applied to the motor 13 based on changes in the current flowing through the motor 13. The pattern of the load torque applied to the motor 13 varies depending on the type of deterioration of the electrode 111, the sliding contact 16, and the motor 13. Based on these differences in patterns, the residual chlorine meter 1 can detect the degree of deterioration for each type of replaceable component, i.e., the electrode 111, the sliding contact 16, and the motor 13.

For example, in the electrode 111 of the indicator electrode 11, it is known that scaly irregularities occur on the surface as the period of use progresses. When scaly irregularities occur on the surface of the electrode 111, it is known that fine waveforms are superimposed on the waveform of the current flowing through the motor 13. Therefore, the residual chlorine meter 1 may learn the waveforms corresponding to such deterioration of the electrode 111 in advance and compare the measured value of the current flowing through the motor 13 with the waveforms learned in advance to detect the degree of deterioration of the electrode 111.

When the electrode 111 of the indicator electrode 11 is new, the measured value of the diffusion current measured by the residual chlorine meter 1 exhibits a waveform that does not depend on the rotation period of the indicator electrode 11. As the period of use progresses, however, the measured value of the diffusion current is known to approach a sinusoidal waveform whose period is the rotation period of the indicator electrode 11. Therefore, the residual chlorine meter 1 may detect the degree of deterioration of the electrode 111 based on the waveform of the diffusion current.

With regard to the sliding contact 16, it is known that as the period of use lengthens, the clearance between the rotating and non-rotating mechanical parts degenerates, and the lubricant that fills the space between the rotating and non-rotating mechanical parts deteriorates, making operations less smooth. The rough operation of the sliding contact 16 can be observed as a phenomenon whereby the load torque increases, increasing the value of the current flowing through the motor 13, despite the indicator electrode 11 being rotated in the same way. Therefore, the residual chlorine meter 1 may detect the deterioration of the sliding contact 16 based on an overall increase in the value of the current flowing through the motor 13 when the same operations are performed. In the sliding contact 16, the brush that causes current to flow between the rotating and non-rotating mechanical parts may deteriorate as the period of use lengthens, causing momentary contact failure to occur periodically at a timing corresponding to the rotation period of the indicator electrode 11. Such contact failure is observed as a periodic interruption, in the sample of the value of current flowing through the motor 13, at a timing corresponding to the rotation period of the indicator electrode 11 or the like. Therefore, the residual chlorine meter 1 may detect the deterioration of the sliding contact 16 based on the periodic interruption of the sample of the value of current flowing through the motor 13.

With regard to the motor 13, the torque output decreases for the same amount of current due to deterioration of the motor bearing part over time, deterioration of the lubricant, and the like. Hence, it is known that the current value required to output the same torque increases. The residual chlorine meter 1 may therefore detect the degree of deterioration of the motor 13 based on an increase in the current value flowing through the motor 13. Due to factors such as deterioration of the bearings forming part of the motor 13, the load torque applied during one rotation of the indicator electrode 11 becomes non-uniform, and a "creaking" or "rumbling" sensation may occur during rotation of the motor 13. Such a sensation appears as a waveform of current, flowing through the motor 13, that rises and falls in accordance with the rotation period of the motor 13. Therefore, the residual chlorine meter 1 may detect the degree of deterioration of the motor 13 based on how the current value flowing through the motor 13 rises and falls in accordance with the rotation period of the motor 13.

As the period of use of the motor 13 lengthens, insulation defects in the electrodes and other components that supply power to drive the motor 13 may occur, causing momentary contact failure to occur periodically at a timing corresponding to the rotation period of the indicator electrode 11. Such contact failure is observed as a periodic interruption, in the sample of the value of current flowing through the motor 13, at a timing corresponding to the rotation period of the indicator electrode 11 or the like. Therefore, the residual chlorine meter 1 may detect the deterioration of the motor 13 based on a periodic interruption in the sample of the value of current flowing through the motor 13.

As described above, the residual chlorine meter 1 detects the deterioration of the electrode 111 based on the measured value of the diffusion current and detects contact failure of the sliding contact 16 and bearing deterioration/contact failure of the motor 13 based on the measured value of the current flowing through the motor 13. The residual chlorine meter 1 bases this detection on periodic fluctuation of the signal. In the present specification, the signal analysis for detecting such periodic variations of signals is referred to as alternating current (AC) analysis (AC-type analysis). Specifically, AC analysis refers to analysis in which specific frequency components are extracted and removed, and specific frequency bands are amplified or otherwise processed. By performing AC analysis on the current or diffusion current of the motor 13, the residual chlorine meter 1 can extract periodic features that occur as each replaceable component changes over time. The residual chlorine meter 1 may perform different AC analysis for each replaceable component. By performing AC analysis, the residual chlorine meter 1 may, for example, extract the "gurgling" sensation of damaged bearings directly as a current waveform and may thereby detect a sign of deterioration. The residual chlorine meter 1 may also detect signs of deterioration by acquiring the waveform of each replaceable component upon deterioration in advance and comparing with the measured current or diffusion current of the motor 13 as appropriate.

On the other hand, the residual chlorine meter 1 detects deterioration of the sliding contact 16, deterioration of the motor bearing portion over time, deterioration of the lubricant, and the like based on an increase in the measured current flowing through the motor 13. In the present specification, the signal analysis for detecting such overall trends in the values of signals is referred to as direct current (DC) analysis (DC-type analysis). Specifically, DC analysis refers to analysis in which integration processing over a specific period of time, calculation of moving averages and medians, and the like are performed. By performing DC analysis on the current or diffusion current of the motor 13, the residual chlorine meter 1 can extract average features that occur as each replaceable component changes over time. The residual chlorine meter 1 may perform different processing for each replaceable component with respect to the setting of the specific period, the selection of processing, and the like. DC analysis may include analog analysis, digital analysis, or a combination thereof. Digital analysis may include advanced analysis such as a Fast Fourier Transform (FFT). For example, in a case in which the grease for the bearings gradually deteriorates and hardens, the load torque of the motor 13 gradually becomes heavier, resulting in a higher average value of the drive current of the motor 13. The residual chlorine meter 1 may perform DC analysis on the current of the motor 13 to detect the increase in the average value of the current of the motor 13 and detect a sign of deterioration. The residual chlorine meter 1 may also set a threshold in advance and determine a sign of deterioration by comparing the value acquired based on DC analysis of the signal with the threshold.

Figure 5:
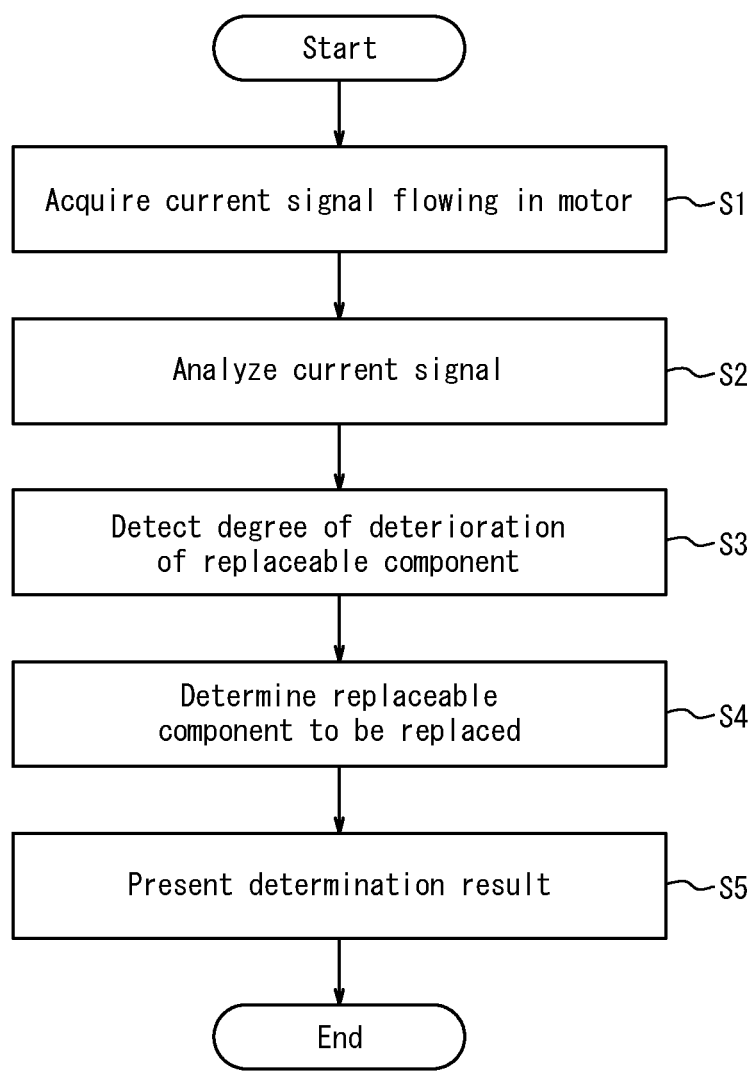
FIG. 5 is a flowchart illustrating an example of processing executed by a residual chlorine meter.

FIG. 5 is a flowchart illustrating an example of processing executed by the residual chlorine meter 1. Operations of the residual chlorine meter 1 described with reference to FIG. 5 correspond to a control method of the residual chlorine meter 1 according to the present embodiment. In the example described below, the controller 53 is the same as the controller 41, and the controller 41 controls the overall operations of the residual chlorine meter 1. Each step in FIG. 5 is executed based on control by the controller 41 in the residual chlorine meter 1. A process to detect the deterioration of a replaceable component based on the current signal flowing through the motor 13 is described below, but the same process is also used in the case of detecting the deterioration of a replaceable component based on the diffusion current.

In step S1, the controller 41 acquires the current signal flowing through the motor 13. Specifically, the controller 41 acquires the signal of the current flowing through the motor 13, the signal having been converted from current to voltage by the resistors 33 to 35 and 37 and the comparator (operational amplifier) 36 and then converted to a digital signal by the analog to digital converter 38. The controller 41 may store data on the acquired current signal in the memory 42 or transfer the data to another information processing apparatus. When executing the process of the flowchart for the first time for the residual chlorine meter 1, the controller 41 may store the data on the current signal acquired in step S1 in the memory 42 as data for the new state.

In step S2, the controller 41 analyzes the current signal acquired in step S1. Specifically, the controller 41 may perform various types of analysis, including the above-described AC analysis, DC analysis, or a combination thereof, on the signal of the current flowing through the motor 13. During the analysis, the controller 41 may remove noise generated by the motor 13, noise generated by a commercial power supply, unwanted noise from external sources, and the like from the signal of the current in the motor 13. Specifically, for example, the controller 41 may remove noise before AD conversion. The controller 41 may store the result of analysis in the memory 42.

In step S3, the controller 41 detects the degree of deterioration of the replaceable component based on the result of analysis of the current signal in step S2. Specifically, the controller 41 may detect the degree of deterioration of a replaceable component by comparing the analysis result in step S2 with the analysis result acquired in advance by machine learning or the like. For example, the controller 41 may detect the degree of deterioration of the replaceable component by storing the analysis result for the current of the motor 13 when the replaceable component is in a new state and comparing the analysis result from step S2 with the stored analysis result. The target of comparison with the analysis result from step S2 may also be the analysis result for the current of the motor 13 acquired in advance for each replaceable component.

In step S4, the controller 41 determines the replaceable component that should be replaced based on the degree of deterioration of the replaceable component detected in step S3. For example, the controller 41 may determine that the replaceable component should be replaced in a case in which the degree of deterioration of the replaceable component detected in step S3 exceeds a predetermined threshold for the degree of deterioration.

In step S5, the controller 41 presents the determination result from step S4 to the user. For example, the controller 41 may display an image indicating the determination result on the display of the output interface 45 or provide audio notification of the determination result. The controller 41 may transmit an e-mail indicating the determination result to a preregistered e-mail address of the device manager. The controller 41 may also notify the user of the degree of deterioration of each replaceable component in addition to whether replaceable components need to be replaced. After completing the process of step S5, the controller 41 ends the process of the flowchart in FIG. 5.

As described above, the residual chlorine meter 1 is an apparatus for measuring the concentration of residual chlorine in sample water W. The residual chlorine meter 1 includes the indicator electrode 11 and the counter electrode 12 to be immersed in the sample water W and the controller 41 that measures the concentration of residual chlorine in the sample water W based on a diffusion current flowing between the indicator electrode 11 and the counter electrode 12 in a case in which a voltage is applied between the indicator electrode 11 and the counter electrode 12. The controller 41 detects the degree of deterioration of a replaceable component of the residual chlorine meter 1 based on a motor current, flowing through the motor 13 that rotates the indicator electrode 11 in the sample water W, and/or the diffusion current. Since the residual chlorine meter 1 thus detects the degree of deterioration of the replaceable component based on the motor current and/or the diffusion current, the user can replace the replaceable component at a more appropriate timing according to the degree of deterioration.

The controller 41 may perform AC-type analysis, which is signal analysis to detect periodic fluctuations, on the motor current and/or the diffusion current. The controller 41 may detect the degree of deterioration of the replaceable component of the residual chlorine meter 1 by comparing the result of the AC-type analysis performed on the motor current and/or the diffusion current with the result of the AC-type analysis on a sample signal acquired in advance. Since the residual chlorine meter 1 thus detects the degree of deterioration of the replaceable component by performing AC-type analysis on the motor current and/or the diffusion current, the residual chlorine meter 1 can appropriately detect deterioration of the replaceable component, which manifests as periodic fluctuations in the motor current or the diffusion current.

The controller 41 may perform DC-type analysis, which is signal analysis to detect an overall trend in values, on the motor current and/or the diffusion current. The controller 41 may detect the degree of deterioration of the replaceable component of the residual chlorine meter 1 by comparing the result of the DC-type analysis performed on the motor current and/or the diffusion current with the result of the DC-type analysis on a sample signal acquired in advance. Since the residual chlorine meter 1 thus detects the degree of deterioration of the replaceable component by performing DC-type analysis on the motor current and/or the diffusion current, the residual chlorine meter can appropriately detect deterioration of the replaceable component, which manifests as overall fluctuations in the motor current or the diffusion current.

The replaceable component may be the motor 13, the electrode 111 of the indicator electrode 11, or the sliding contact 16 for extracting the diffusion current from the indicator electrode 11. The residual chlorine meter 1 is therefore capable of detecting deterioration with respect to the motor 13, the electrode 111 of the indicator electrode 11, and the sliding contact 16. In addition to the motor 13, the electrode 111 of the indicator electrode 11, and the sliding contact 16, the residual chlorine meter can also detect the deterioration of the beads 233 as the replaceable component, for example, and determine whether the beads 233 need to be replaced.

The controller 41 may determine whether the replaceable component should be replaced based on the detected degree of deterioration and present the result of determining whether the replaceable component should be replaced to the user. For example, the controller 41 may display an image indicating the determination result on the display of the output interface 45 or provide audio notification of the determination result. Accordingly, the user can easily grasp whether the replaceable component needs to be replaced.

The controller 41 may automatically perform steps S1 to S5 periodically (for example, once a week, once a month, or the like). This enables the residual chlorine meter 1 to periodically monitor the state of deterioration of the replaceable component and immediately notify the user if the replaceable component needs to be replaced.

Second Embodiment

The residual chlorine meter 1 may transmit the current or diffusion current flowing through the motor 13 to another information processing apparatus, and the other information processing apparatus may analyze the data.

Figure 6:
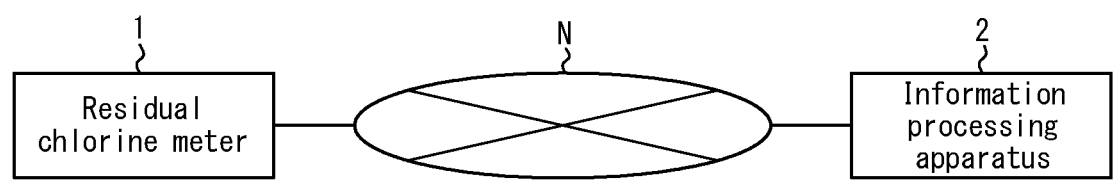
FIG. 6 is a diagram illustrating an example configuration of a chlorine meter system according to an embodiment.

A chlorine meter system 3 that performs such processing is now described with reference to FIG. 6. FIG. 6 is a diagram illustrating an example configuration of the chlorine meter system 3 according to an embodiment.

The chlorine meter system 3 includes a residual chlorine meter 1 and an information processing apparatus 2. The residual chlorine meter 1 and the information processing apparatus 2 can communicate with each other via a network N. The residual chlorine meter 1 has the same configuration as the residual chlorine meter of the first embodiment. The information processing apparatus 2 is any information processing apparatus, such as a personal computer (PC), workstation (WS), tablet, or cloud server. The network N is a wired network, a wireless network, or a combination thereof.

Upon acquiring the current or diffusion current of the motor 13, the residual chlorine meter 1 transmits the data to the information processing apparatus 2 via the network N. In other words, the residual chlorine meter 1 transmits the data on the current or diffusion current of the motor 13 to the information processing apparatus 2 by, for example, wireless or wired communication. The information processing apparatus 2 analyzes the received data, detects the degree of deterioration of the replaceable component, and determines whether replacement is necessary. Specifically, the information processing apparatus 2 executes the processes of steps S1 to S5 of FIG. 5. In this way, in the chlorine meter system 3, the information processing apparatus 2 detects the degree of deterioration of the replaceable component based on the motor current and/or the diffusion current and determines whether the replaceable component should be replaced. Therefore, even if the residual chlorine meter 1 is not equipped with a data analysis capability, the user can know whether the replaceable component should be replaced based on the degree of deterioration of the replaceable component and can replace the replaceable component at a more appropriate timing.

As described above, according to each embodiment of the present disclosure, the drive current or diffusion current that is proportional to the load torque of the motor 1 is analyzed to predict the deterioration of each replaceable component. Therefore, the residual chlorine meter 1 or the information processing apparatus 2 can accurately determine the state of deterioration of each replaceable component and notify the user accordingly at an appropriate timing. Upon receiving the notification, the user can replace the replaceable component at the necessary and efficient timing.

The present disclosure is not limited to the above embodiments. For example, a plurality of blocks described in the block diagrams may be integrated, or a block may be divided. Instead of a plurality of steps described in the flowcharts being executed in chronological order in accordance with the description, the plurality of steps may be executed in parallel or in a different order according to the processing capability of the apparatus that executes each step, or as required. Other modifications can be made without departing from the spirit of the present disclosure.

The invention claimed is:

1. A residual chlorine meter for measuring a concentration of residual chlorine in sample water, the residual chlorine meter comprising:
   an indicator electrode and a counter electrode to be immersed in the sample water; and
   a controller configured to measure the concentration of residual chlorine in the sample water based on a diffusion current flowing between the indicator electrode and the counter electrode in a case in which a voltage is applied between the indicator electrode and the counter electrode, wherein
   the controller is configured to:
      perform AC-type analysis on the diffusion current, while applying a DC voltage between the indicator electrode and the counter electrode, wherein the AC-type analysis is a signal analysis to detect periodic fluctuations corresponding to a rotation period of the indicator electrode; and
      detect a degree of deterioration of a replaceable component of the residual chlorine meter based on a result of the AC-type analysis performed on the diffusion current,
      wherein the replaceable component is a sliding contact for extracting the diffusion current from the indicator electrode.

2. The residual chlorine meter according to claim 1, wherein the controller is configured to detect the degree of deterioration of the replaceable component of the residual chlorine meter by comparing the result of the AC-type analysis performed on the diffusion current with a result of the AC-type analysis on a sample signal acquired in advance.

3. The residual chlorine meter according to claim 1, wherein the controller is configured to
   further perform DC-type analysis, which is signal analysis to detect an overall trend in values, on a motor current, flowing through a motor that rotates the indicator electrode in the sample water, and/or the diffusion current, and
   detect the degree of deterioration of the replaceable component of the residual chlorine meter by comparing a result of the DC-type analysis performed on the motor current and/or the diffusion current with a result of the DC-type analysis on a sample signal acquired in advance.

4. The residual chlorine meter according to claim 1, wherein the controller is configured to
   determine whether the replaceable component should be replaced based on the detected degree of deterioration, and
   present a result of determining whether the replaceable component should be replaced to a user.

5. A control method for the residual chlorine meter according to claim 1, the control method comprising:
   detecting, by the controller, the degree of deterioration of the replaceable component of the residual chlorine meter based on the diffusion current.

6. The residual chlorine meter according to claim 1, wherein the controller is configured to detect the degree of deterioration of the replaceable component of the residual chlorine meter based on a waveform of the diffusion current.

7. The residual chlorine meter according to claim 1, wherein the controller is configured to detect the degree of deterioration of the replaceable component of the residual chlorine meter by comparing a waveform of the measured diffusion current with a waveform of a diffusion current of the replacement component upon deterioration acquired in advance.

8. A residual chlorine meter for measuring a concentration of residual chlorine in sample water, the residual chlorine meter comprising:
   an indicator electrode and a counter electrode to be immersed in the sample water; and
   a controller configured to measure the concentration of residual chlorine in the sample water based on a diffusion current flowing between the indicator electrode and the counter electrode in a case in which a voltage is applied between the indicator electrode and the counter electrode, wherein
   the controller is configured to detect a degree of deterioration of a replaceable component of the residual chlorine meter based on the diffusion current, and
   the replaceable component is a sliding contact for extracting the diffusion current from the indicator electrode.

* * * * *